United States Patent [19]

Steen

[11] Patent Number: 5,684,575
[45] Date of Patent: Nov. 4, 1997

[54] OPTICAL ARRANGEMENT FOR FLOW CYTOMETER TO FACILITATE LARGE ANGLE LIGHT-SCATTERING MEASUREMENT

[76] Inventor: Harald Steen, Wolffsgt. 3, N-0358 Oslo, Norway

[21] Appl. No.: 522,396

[22] PCT Filed: Mar. 16, 1994

[86] PCT No.: PCT/NO94/00059

§ 371 Date: Sep. 18, 1995

§ 102(e) Date: Sep. 18, 1995

[87] PCT Pub. No.: WO94/22001

PCT Pub. Date: Sep. 29, 1994

[30] Foreign Application Priority Data

Mar. 18, 1993 [NO] Norway ............... 930980

[51] Int. Cl.$^6$ .................................................. G01N 21/00
[52] U.S. Cl. .............................................. 356/73; 356/73
[58] Field of Search .................................. 356/73, 72

[56] References Cited

U.S. PATENT DOCUMENTS

| | | | |
|---|---|---|---|
| 4,500,641 | 2/1985 | van den Engh et al. | 356/318 |
| 4,690,561 | 9/1987 | Ito | 356/73 |
| 4,957,363 | 9/1990 | Takeda et al. | 356/73 |
| 5,050,987 | 9/1991 | Kosaka | 356/73 |
| 5,123,731 | 6/1992 | Yoshinaga et al. | 356/73 |
| 5,162,863 | 11/1992 | Ito | 356/73 |
| 5,185,265 | 2/1993 | Steen et al. | 356/73 |
| 5,444,527 | 8/1995 | Kosaka | 356/73 |

FOREIGN PATENT DOCUMENTS

| | | |
|---|---|---|
| 62-245942 | 10/1987 | Japan. |
| 1-196536 | 8/1989 | Japan. |
| 8700628 | 1/1987 | WIPO. |

*Primary Examiner*—Frank G. Font
*Assistant Examiner*—Jason D. Viena Eisenberg
*Attorney, Agent, or Firm*—Cushman Darby & Cushman Intellectual Property Group of Pillsbury Madison & Sutro LLP

[57] ABSTRACT

An optical arrangement for a flow cytometer, wherein intense light is focused by a microscope objective having a numerical aperture $Na_i$, onto the cells carried by a flow of water through the focal plane of the objective, with another microscope lens situated opposite the objective, with an optical axis and object plane coinciding with the objective and with a numerical aperture, $NA_O$, which is significantly larger than that of the objective. The objective contains a circular field stop in, or close to, its secondary focal plane, with a diameter corresponding to a numerical aperture $NA_{sp}$, which is slightly larger than $NA_i$, and much less than $NA_O$. The fluorescence and scattered light from the stream of cells are separated by a dicroic mirror on basis of their different wavelength, so that they give rise to separate images in separate image planes of the objective. A telescope is situated behind the image plane and creates an image of the field stop in a plane with two concentric mirrors of different diameters, which separate light scattered from the cells according to the different scattering angles and direct them onto separate light detectors.

4 Claims, 1 Drawing Sheet

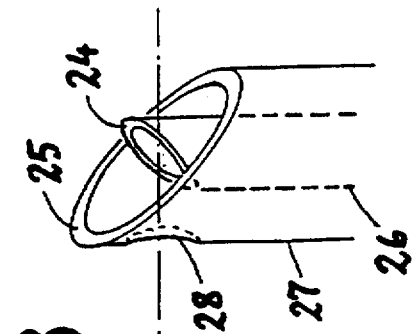
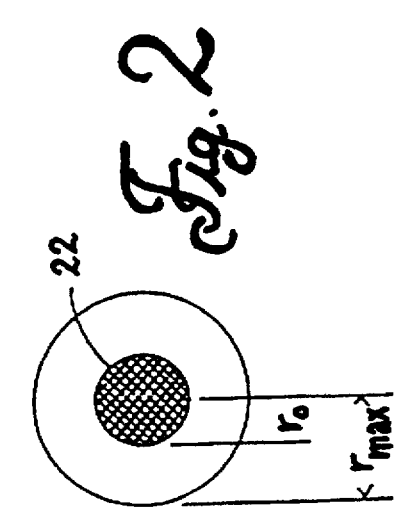
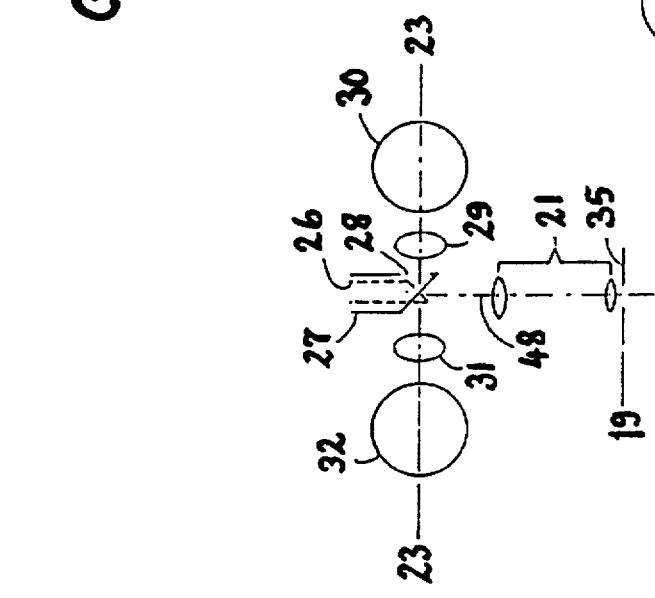
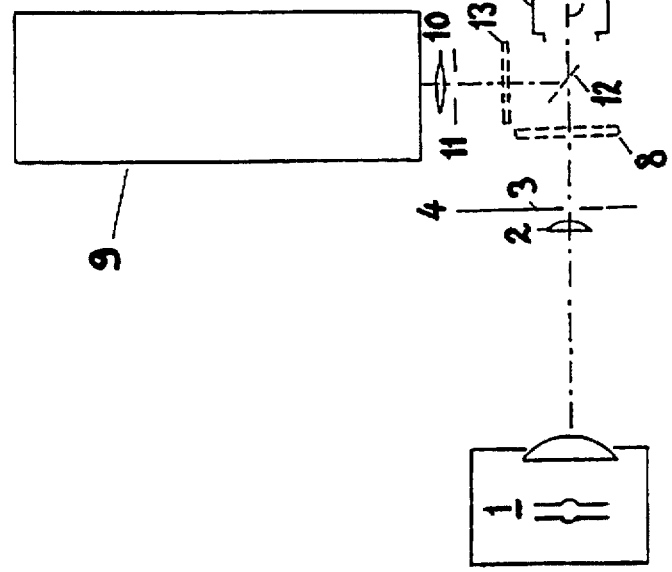

OPTICAL ARRANGEMENT FOR FLOW CYTOMETER TO FACILITATE LARGE ANGLE LIGHT-SCATTERING MEASUREMENT

BACKGROUND OF THE INVENTION

The present invention relates to an optical arrangement for flow cytometers.

A flow cytometer is an instrument for measurement of the fluorescence and light scattering of individual biological cells and other types of microscopical particles. In the flow cytometer, the cells are carried by a laminar flow of water through the focus of a high intensity light source. The cells are typically stained with a fluorescent dye which binds specifically to one particular cell constituent. Each cell passing through the focus will thus emit a short pulse of fluorescence and scattered light. The intensity of the fluorescence will be proportional to the cellular content of fluorescent dye and thereby with the cellular content of the stained constituent. The intensity of the scattered light and its angular distribution is a complex function of the size, shape, structure and chemical composition of the cell. By measuring with separate detectors the light scattering at small and large scattering angles, respectively, it is thus possible to distinguish cells on the basis of size, shape, and structure.

For some purposes, the cells may be stained by two or three different dyes which bind to different cellular constituents and fluoresce at different wavelengths. The corresponding spectral components of the fluorescence can be separated by dichroic mirrors and band filters and measured by separate detectors. Hence, each cell may generate several signals; typically two light scattering signals—low and large angle scattering—and two or three fluorescence signals. This technology is well known and has been published in many articles, e.g. in "Flow cytometry and sorting" (Melamed, M. R.; Lindmo, T; Mendelsohn, M. L., Eds.), Wiley-Liss, New York 1990.

The cellular content of the constituent(s) to be measured may be quite small, that is down to about $1 \cdot 10^{-18}$ g/cell. The demands on the sensitivity of the instrument are correspondingly high. In order to achieve such sensitivity the excitation light has to be concentrated into a very small and correspondingly intense focus. Furthermore, the optics which collects the fluorescence and scattered light must have the highest possible numerical aperture. It is essential also that any light from other sources than the cells, e.g. the background due to fluorescence and light scattering from optics and other components in the optical path, is as low as possible.

There are two major types of flow cytometers: a) Instruments employing a laser as the source of excitation light, and b) instruments using a high pressure arc lamp with xenon or mercury. The laser-based instruments have the advantage that the excitation light can be focused into a very small and correspondingly intense focus. Furthermore, the beam of excitation light is near parallel, which simplifies the distinction of light scattered to different angles. Arc lamp-based instruments have the advantage that the spectrum of the light source contains all wavelengths from UV through the visible spectrum. Hence, by means of appropriate filters the proper wavelength for excitation of any fluorescent dye can be selected, thus making this type of instruments more versatile.

All laser-based flow cytometers have essentially the same optical configuration, namely so that the vertical sample stream cuts through the focus of a horizontal laser beam and so that this focus is intersected at a 90 degree angle by the optical axis of the optics which collects the fluorescence and the light scattered to large angles, i.e. around 90°. Behind the light collecting optics fluorescence and light scattering are separated by a dichroic mirror and directed onto separate light detectors. The fluorescence may be further split into different spectral components by additional dichroic mirrors and measured by separate detectors.

The light of the focused laser beam is near parallel, that is falling within a light cone of about 2° or less. Hence, the light scattering at low scattering angles is measured through an other lens with its optical axis coincident with the laser beam. The laser beam is prevented from entering the lens by a field stop situated in front of the lens.

Some laser-based flow cytometers employ two lasers emitting at different wavelengths and focused to separate foci, so that the cells are excited sequentially with two different wavelengths. Thus, it becomes possible to measure two different dyes which cannot be excited by the same wavelength or which interfere in ways which are not compatible with the measurement. Such "two focus excitation" has many interesting biological applications.

All arc lamp-based flow cytometers employ epi-illumination, which is to say that the optics which concentrate the light in the excitation focus, also collects the fluorescence. In order to achieve the highest possible excitation intensity as well as optimal fluorescence collection efficiency, this optics should have the highest possible numerical aperture (NA). Hence, an oil immersion microscope lens, having NA$\approx$1,3, is used for this purpose.

The large field angle of the illumination field of such a lens makes it impossible to distinguish the light scattering at small and large scattering angles by the same type of optical configuration as that usede in the laser-based instruments. The Norwegian patents Nos. 145.176 and 156.917, as well as U.S. Pat. Nos. 4,408,877 and 4,915,501 disclose how light scattering can be measured in the epi-illumination type of optical configuration used in arc lamp-based instruments. By means of a central field stop close to the back focal plane of this lens, a dark field is created which allows measurement of light scattering at both small and large scattering angles through a second microscope lens situated opposite to the first and with its aperture within the dark field produced by the field stop in the first lens.

However, this configuration has certain shortcomings. Thus, it allows the light scattering at large angles to be measured only within a very small aperture, i.e. NA$\geq$0,04. This small aperture limits the sensitivity of the measurement of this parameter. Furthermore, with this configuration the "large angle" range has a lower limit which does not exceed about 20°.

Another disadvantage of the epi-illumination configuration of current arc lamp-based flow cytometers is that it does not allow excitation in two separate loci of different wavelength, thus, limiting to some extent the range of applications of such instruments. The epi-illumination also implies that the optics which collects the fluorescence, i.e. the microscope objective, is exposed to very high intensities of excitation light. Even with microscope objectives of the very highest quality this is causing some fluorescence from the elements of the objective which adds to the background on which the cell fluorescence is detected, and thereby to a reduction of the signal to noise ratio, which is equivalent to a reduction of the sensitivity.

SUMMARY OF THE INVENTION

The present invention is a novel optical configuration which eliminates some of the above mentioned limitations of current designs of arc lamp-based flow cytometers. Thus, the present invention facilitates large angle light scattering measurement at considerably higher scattering angles and with a much higher numerical aperture than was feasible with the previous configuration. Hence, the light scattering sensitivity is considerably increased relative to current designs. It also produces less background light in the fluorescence light path, and allows "two focus excitation".

More specifically, the present invention provides an optical arrangement for flow cytometer, wherein intense light is focused by a microscope objective or similar lens having a numerical aperture $NA_1$ onto a stream of cells carried by a laminar flow of water through the focal plane of said objective; and wherein another microscope lens is situated opposite to the objective, and with its optical axis and object plane coinciding with those of said objective, and with a numerical aperture, $NA_O$, which is significantly larger than that of said objective; wherein said objective contains a circular central field stop in, or close to, its secondary focal plane, said field stop having a diameter corresponding to a numerical aperture, $NA_{fp}$, which is slightly larger than $NA_i$, while it is much less than $NA_O$, so that the illumination field of the objective falls entirely within said field stop, and hence so that the image of the stream of cells created by the objective contains only fluorescence and scattered light from the stream of cells; wherein the fluorescence and scattered light from the stream of cells are separated by a dichroic mirror on basis of their different wavelength, so that the fluorescence and scattered light give rise to separate images of the stream of cells in separate image planes of the objective; and wherein a telescope, situated immediately behind the image plane creates an image of said field stop in a plane, where is situated two concentric mirrors, of different diameter, which separate light scattered from the stream of cells to different scattering angles and direct the scattered light of different scattering angles onto separate light detectors.

According to a further feature of the invention, the stream of cells coincides with the object plane of the objectives, and the stream of cells is illuminated through the objective in one or two adjacent foci of different wavelength emitted by two separate light sources.

According to another feature of the invention first and second slits may cover the image of each of the adjacent foci from said light sources in the object plane, so that fluorescence measured behind the first slit originates from only one of said foci whereas fluorescence measured behind the second slit originates only from the other of the foci.

According to yet another feature of the invention, the mirrors in the image plane of the telescope are flat, polished end planes that are cut at an angle of 45° of two concentric tubes having their common axis coinsiding with the optical axis of the telescope.

BRIEF DESCRIPTION OF THE DRAWING

The invention is now to be described with reference to a preferred, non-limitative embodiment of the invention illustrated in the attached drawing, in which:

FIG. 1 shows the optical arrangement for flow cytometers, according to the invention;

FIG. 2 shows more detailed a telescope formed image, according to the invention;

FIG. 3 shows a concentric mirror embodiment, according to the invention.

DETAILED DESCRIPTION

The invention, shown schematically in FIGS. 1, 2 and 3, is a device which contains a light source 1 which, through a lens 2, illuminates an excitation slit 3, which is situated in the image plane 4 of a microscope objective or similar lens 5 which concentrates the excitation light from the light source 1 in an excitation focus 6 in the object plane 7 of the objective 5. An interference band filter 8 is situated in the light path behind the objective 5 in order to isolate the appropriate wavelength of excitation.

The device can also include a secondary light source 9 which, through a lens 10, illuminates an excitation slit 11. An image of this slit 11 is formed by the lens 5 in the image plane 7 via a dichroic mirror 12. An interference filter 13 isolates a band of excitation wavelength, preferably not overlapping that of the band filter 8. The excitation slits 3 and 11 are situated so that their images in the object plane 7 do not overlap, but are closely adjacent on each side of the optical axis 14 of the lens 5.

The sample stream, containing cells or other microscopical particles to be measured, is conducted by the measuring chamber 15 in the object plane 7 through the optical axis 14 of the lens 5.

Another microscope objective 16, preferably of the oil immersion type with a numerical aperture of approximately NA=1.3, is situated opposite the lens 5 so that the two objectives 5 and 16 have their respective optical axis 14 and respective object plane 7 coinciding.

Inside said objective 16 is a central, circular field stop 17, with its center in the optical axis 14 and in a plane which is close to the back focal plane of the objective 16. The field stop 17 covers the central part of the aperture of the objective 16, thus stopping light falling within a solid angle corresponding to a numerical aperture, $NA_{fp}$, which is just slightly larger than the numerical aperture, $NA_i$, of the lens 5. Hence, excitation light focused onto the object plane 7 by the lens 5 is not transmitted by the objective 16. Consequently, the light collected by the objective 16 will contain only fluorescence and scattered light from the sample stream through the measuring chamber 15. Behind the objective 16 is situated a dichroic mirror 18 with a characteristic wavelength so that said scattered light is reflected to form an image of said sample stream in an image plane 19 of the objective 16, whereas the fluorescence is transmitted to form a corresponding image in the image plane 20 of the objective 16.

Behind the image plane 19 is a telescope 21 which forms an image, as shown in FIG. 2, of the plane containing the field stop 17 in a plane 23. Outside the dark field 22, which is the image of the field stop 17, is light scattered from cells in the sample stream. It will be understood that light falling at a given distance, r, from the center of the image in the plane 23 is emitted with scattering angles exceeding a certain limit, $\alpha_1$ (Eq. 1) and below an upper limit, $\alpha_2$ (Eq. 2).

$$\alpha_1 = \arcsin[(r/r_O)(NA_{fp}/n)] - \arcsin(NA_i/n) \qquad \text{Eq.(1)}$$

$$\alpha_2 = \arcsin[(NA_O + NA_i)/n] \qquad \text{Eq.(2)}$$

where n is the refractive index of the sample stream, usually water, and $r_O$ the radius of the image 22 of said field stop 17, as determined by the magnification of the telescope 21.

It can be seen that the lowest scattering angle which can be detected in the image plane 23, that is, at the periphery of the image 22 of the field stop 17 where $r=r_O$, is given by:

$$\alpha_1(min) = \arcsin(NA_{fp}/n) - \arcsin(NA_i/n) \qquad \text{Eq.(3)}$$

The largest scattering angle that can be detected, i.e. at the outer periphery of the image (FIG. 2) in the image plane 23, where:

$$r=r(max)=r_O(NA_O/NA_{\varphi}) \quad \text{Eq.(4)}$$

is given by:

$$\alpha_1(max)=\arcsin(NA_O/n)-\arcsin(NA_i/n) \quad \text{Eq.(5)}$$

The theory of light scattering from microscopical particles as well as experimental data on this phenomenon shows that the intensity of the scattered light falls off very rapidly with increasing scattering angle over the entire range from 0 to about 60°. Hence, a light scattering signal collected over a certain range of scattering angles will be strongly dominated by scattering from angles close to the lower limit of this range. Thus, a light scattering signal collected just outside the periphery of the image 22 of the field stop 17, to a good approximation will represent low scattering angles, that is angles just above $\alpha_1$(min); whereas light collected close to the outer periphery contains only light from large scattering angles, that is, upwards from about $\alpha_1$(max).

A suitable value for $NA_i$ is 0,60, whereas $NA_{\varphi}$=0,62 and $NA_O$=1,3. According to Eqs. 3 and 5, these values give: $\alpha_1$(min)=0,97° and $\alpha_1$(max)=51°.

The two light scattering components representing low and large scattering angles, respectively, are directed onto separate light detectors by means of two concentric mirrors 24 and 25 (FIG. 3) formed by the plane, polished front surfaces of two cylindrical tubes which are cut at 45° to their axis and which are coaxial with the optical axis of the telescope 21. Said mirrors 24 and 25 face in opposite directions, as shown in FIG. 3. The inner tube 26 has an inner diameter equal to $r_O$, while the inner diameter of the outer tube 27 is a little less than $r_{max}$. Said mirrors 24 and 25 both have their center in the image plane 23 The outer tube 27 has an opening 28 in that side which is facing the mirror 24, so that the light reflected by the mirror 24 can pass through the opening 28 and through a lens 29 to reach the detector 30. The light reflected from the mirror 25 is directed through a lens 31 onto a detector 32.

Between the dichroic mirror 18 and the image plane 20 is another dichroic mirror 33 which directs certain wavelengths of fluorescence, usually shorter wavelengths, to form an image from the objective 16 in the plane 34, whereas fluorescence of other wavelengths, usually longer, is transmitted to form an image in the plane 20. Thus, the device exhibits three separate image planes 19, 20 and 24 for the objective 16, wherein the same image is formed in three different regions of wavelength. In each of the image planes 19, 20, and 24 is situated a rectangular slit, the size of which can be varied so as to match the size of the image of the illuminated part of the stream of cells in the flow chamber 15 in order to eliminate light from other parts of the object plane 7 and thereby suppress background light which otherwise reduces the signal to noise ratio of the light detection and thereby the sensitivity.

Dichroic mirrors 38 and 39 and optical hand filters 40, 41, 42 and 43 are situated behind the slits 36 and 37 in order to separate different spectral components of the fluorescence and direct these spectral components onto separate detectors 44, 45, 46 and 47.

The dichroic mirror 18 is chosen so as to separate the scattered light, which is reflected, from the fluorescence which is transmitted because of its longer wavelength. The dichroic mirror 33 separates the fluorescence into two different spectral components, each of which is further separated by the dichroic mirrors 38 and 39. Thus, the present device can measure four different fluorescence components. This method of separating different spectral components of fluorescence is well known from the literature, e.g. "Flow cytometry and sorting", Melamed et al, Wiley-Liss, New York 1990. It is trivial to increase the number of fluorescence spectral components further by the addition of more dichroic mirrors and band filters.

An important feature of the invention is that it facilitates so-called "two focus excitation". Light from two separate light sources 1 and 9 is passed through different band pass filters 8 and 13 which transmit two different spectral bands of excitation light. The optical axis of these two spectral bands are somewhat shifted relative to each other so that the objective 5 forms two adjacent excitation foci in the object plane 7. Hence, the cells will pass sequentially through the two excitation foci. The slits 36 and 37 are situated so that they cover the image of each of the two excitation foci. Hence, the fluorescence emitted from each of said excitation foci is separated from each other and can thus be measured by separate detectors.

In the case that such "two focus excitation" is employed, one of the fluorescence detectors, for example 44 or 47 may be used to measure the scattered light from cells excited in that of the excitation loci which has the largest excitation wavelength. The invention thus facilitates measurement of scattered light at two different wavelengths and may thereby provide further information about the cells that are being measured.

I claim:

1. An optical arrangement for a flow cytometer, comprising:
    an intense light focused by an objective having a numerical aperture $Na_i$, onto a stream of cells carried by a laminar flow of water through the focal plane of said objective;
    a microscope lens situated opposite to said objective, with its optical axis and object plane coinciding with those of said objective, and having a numerical aperture $NA_O$, which is significantly larger than that of said objective;
    said microscope lens containing a circular central field stop disposed substantially in its secondary focal plane, said field stop having a diameter corresponding to a numerical aperture $NA_{\varphi}$, which is slightly larger than $NA_i$, while being much less than $NA_O$, so that the illumination field of said objective falls entirely within said field stop, and hence so that the image of said stream of cells created by said microscope lens contains only fluorescence and scattered light from said stream of cells;
    said fluorescence and scattered light from said stream of cells being separated by a dichroic mirror on basis of their different wavelength, so that said fluorescence and scattered light give rise to separate images of said stream of cells in separate image planes of said microscope lens;
    two separate light detectors;
    a telescope situated immediately behind said image plane and creating an image of said field stop in a telescope image plane and
    two concentric mirrors, of different diameter, situated in said telescope image plane and separating light scattered from said stream of cells to different scattering angles and directing said scattered light of different scattering angles onto said two separate light detectors.

2. The arrangement according to claim 1, wherein:
    said stream of cells coincides with said object plane of said objective and microscope lens; and
    said stream of cells is illuminated through said objective in two adjacent foci of different wavelengths emitted by two separate light sources.

3. The arrangement according to claim 2, wherein:

first and second slits cover the image of each of said adjacent loci from said light sources in said object plane, so that fluorescence measured behind said first slit originates from only one of said foci, whereas fluorescence measured behind said second slit originates only from the other of said foci.

4. The arrangement according to claim 1, wherein:

said mirrors in said telescope image plane are flat, polished end planes that are cut at an angle of 45°, of two concentric tubes having their common axis coinciding with the optical axis of said telescope.

* * * * *